United States Patent [19]
Kung et al.

[11] Patent Number: 5,662,643
[45] Date of Patent: Sep. 2, 1997

[54] LASER WELDING SYSTEM

[75] Inventors: Robert T. V. Kung, Andover; Robert B. Stewart, Ipswich; Meir Rosenberg, Newton, all of Mass.

[73] Assignee: Abiomed R & D, Inc., Danvers, Mass.

[21] Appl. No.: 314,191

[22] Filed: Sep. 28, 1994

[51] Int. Cl.$^6$ .............................. A61B 17/32; A61N 5/06
[52] U.S. Cl. ........................ 606/3; 606/8; 606/9; 606/11
[58] Field of Search .............................. 606/2, 3, 10, 11, 606/12, 17

[56] References Cited

U.S. PATENT DOCUMENTS

| | | |
|---|---|---|
| 4,976,709 | 12/1990 | Sand . |
| 5,002,051 | 3/1991 | Dew et al. ............................ 606/12 |
| 5,071,417 | 12/1991 | Sinofsky . |
| 5,169,396 | 12/1992 | Dowlatshahi et al. .................. 606/15 |
| 5,207,670 | 5/1993 | Sinofsky . |
| 5,222,953 | 6/1993 | Dowlatshashi ........................ 606/15 |
| 5,269,778 | 12/1993 | Rink et al. . |
| 5,334,016 | 8/1994 | Goldsmith et al. ...................... 606/10 |
| 5,334,191 | 8/1994 | Poppas et al. .......................... 606/12 |
| 5,350,376 | 9/1994 | Brown .................................. 606/12 |
| 5,569,239 | 10/1996 | Sinofsky ............................... 606/8 |
| 5,571,216 | 11/1996 | Anderson ............................ 606/8 X |

OTHER PUBLICATIONS

Popp et al. (1989), "Welding of Gallbladder Tissue With A Pulsed 2.15 μm Thulium–Holmium–Chromium: YAG Laser", *Lasers in Surgery and Medicine*, vol. 9, pp. 155–159.

Zelt et al. (1991), "Arterial Laser Welding With A 1.9 Micrometer Raman–Shifted Laser", *Journ. of Vascular Surgery*, vol. 15, pp. 1025–1030.

Springer et al. (1993), "Temperature Control During Laser Vessel Welding", *Applied Optics*, vol. 32, pp. 517–525.

Anderson et al. (1993), "Lasers in Otolaryngology, Dermatology, And Tissue Welding", *SPIE*, vol. 1876, pp. 202–209.

Kung et al. (1993), "Absorption Chracteristics at 1.9 μm: Effect On Vascular Welding", *Lasers in Sugery and Medicine*, vol. 13, pp. 12–17.

*Primary Examiner*—Lee S. Cohen
*Assistant Examiner*—Sonya Harris-Ogugua
*Attorney, Agent, or Firm*—Lahive & Cockfield, LLP

[57] ABSTRACT

A laser welding apparatus and system for surgically bonding tissue together provides a beam of coherent light at a wavelength corresponding to a specific tissue thickness at which full absorption of the laser energy occurs, and adjusts the energy of the laser beam in response to tissue temperature throughout the tissue thickness to prevent the tissue temperature from either exceeding a predetermined limit or varying outside a predetermined range. Preferably, the coherent light beam has a center wavelength of 1.9 μm, and is variable between 1.85 and 1.91 μm.

20 Claims, 3 Drawing Sheets

LASER WELDING SYSTEM

BACKGROUND OF THE INVENTION

The present invention relates to surgical apparatus and methods for the treatment of tissue by application of light energy, and particularly to the area of laser surgery wherein tissue is welded or bonded together under controlled temperature conditions.

According to well known surgical techniques, tissue is connected together with suturing materials such as silk, synthetic thread, or metal staples, and then allowed to permanently bind together by the normal healing process. One of the drawbacks, however, of joining tissue with suturing materials is the introduction of foreign material into the tissue. The foreign material may cause intimation, infection and scarring. Additionally, bonding tissue together with suturing material does not create a fluid tight seal. Laser welding tissue together, in comparison, creates a fluid tight seal and does not introduce foreign material into the tissue.

A variety of laser systems have been used for welding tissue, including, Argon, milliwatt $CO_2$, and neodymium doped yttrium aluminum garnet (Nd:YAG) lasers. Each of these lasers is generally understood to cause tissue heating that produces structural changes in tissue, thereby causing cross-linking of proteins and binding of the tissue. As currently practiced, the laser is directed onto the tissue for a time period and with a specified power until subjective tissue changes occur, such as blanching, browning, or shrinking.

Relying on subjective factors to determine the appropriate exposure time and power setting requires considerable experience and instinct. Furthermore, once these changes in the tissue become apparent (i.e. blanching, browning, or shrinking), some damage to the tissue has already occurred. An advantageous system would weld the tissue together without causing the tissue temperature to rise to a burning point.

Another drawback to laser welding as currently practiced, is the failure to match laser wavelengths to respective tissues in order to achieve full absorption of the laser energy with the resulting increased weld strength. For example, Rink et al., U.S. Pat. No. 5,269,778, discloses a variable pulse width laser for ablating the surface of the target tissue without affecting the underlying tissue. As a result, when the laser penetration depth is less than the depth of the selected tissue the laser energy is deposited superficially on the selected tissue, causing excessive heating and possibly charring at the outer tissue surface, and incomplete fusion at further depths. Alternatively, when the laser penetration depth, or optical absorption depth, exceeds the depth of the selected tissue only a small fraction of the energy from the laser is absorbed by the tissue. This creates a need for higher laser intensities and longer exposure times to attain a suitable fusion temperature, in addition, any energy not deposited at the weld site may result in uncontrolled damage to surrounding tissue.

There are further drawbacks to current laser welding systems. For example, the wavelength of the milliwatt $CO_2$ laser is too long to allow the laser energy to be transmitted via silica fiber optics. Instead, a series of mirrors in an articulating arm is required which is cumbersome and difficult to use. Other systems utilize Argon lasers, but these lasers generate high temperatures in the surrounding tissues that require continuous saline irrigation to maintain a narrow welding temperature range and prevent tissue desiccation. As a result, both the $CO_2$ and Argon laser welding systems require complicated and expensive machinery and a great deal of training to implement.

SUMMARY OF THE INVENTION

Accordingly, it is an object of the present invention to provide a laser welding system of improved construction that can produce controlled heating of the tissue substantially throughout the thickness of the tissue.

This is accomplished according to a principal aspect of the invention by providing a coherent beam of light at a predetermined wavelength corresponding to a specific thickness of tissue at which substantially full absorption of the laser energy occurs, without allowing the temperature anywhere in the subject tissue to exceed a predetermined tissue temperature or to range outside a specified range of tissue temperature. In a preferred embodiment, the beam of light has a center wavelength of 1.9 μm, and is variable between 1.85 and 1.91 μm, to allow for matching of tissues of differing thickness. The temperature of the subject tissue is controlled by sensing the tissue temperature and altering the energy of the laser beam in response to the sensed temperature. Since the wavelength and tissue thickness are matched to provide for essentially full absorption within the tissue, the temperature throughout the tissue is substantially constant and the sensed temperature at the surface is then representative of the temperature throughout the depths of the tissue.

BRIEF DESCRIPTION OF DRAWINGS

These and other features of the invention will be understood from the following disclosure, the teachings of which will be read in light of the background technology as understood by a person of ordinary skill in the art, and the illustrations of representative embodiments, wherein.

DETAILED DESCRIPTION OF THE INVENTION

Figure 1:
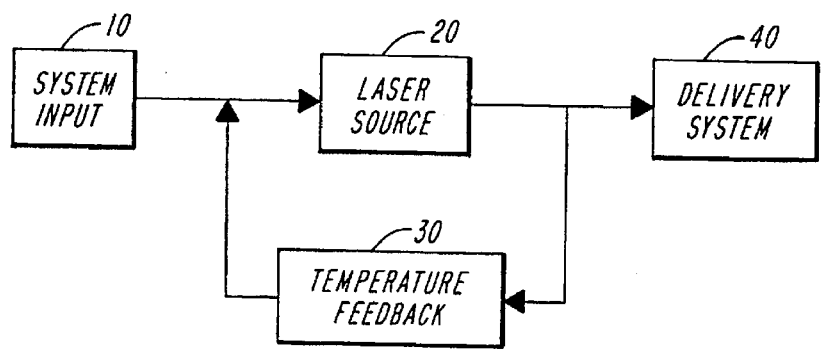
FIG. 1 shows a laser system according to the present invention.

FIG. 1 illustrates a surgical system 1 according to the invention having system input 10 coupled to laser source 20 coupled to delivery system 40 and temperature feedback loop 30. Input block 10 represents user defined parameters for varying the wavelength of coherent light produced by laser source 20. Feedback loop 30 manipulates the coherent light energy produced by laser source 20 to maintain a temperature either below a predetermined value or within a predetermined range. System block 40 aids in delivering the coherent light beam.

Figure 2:
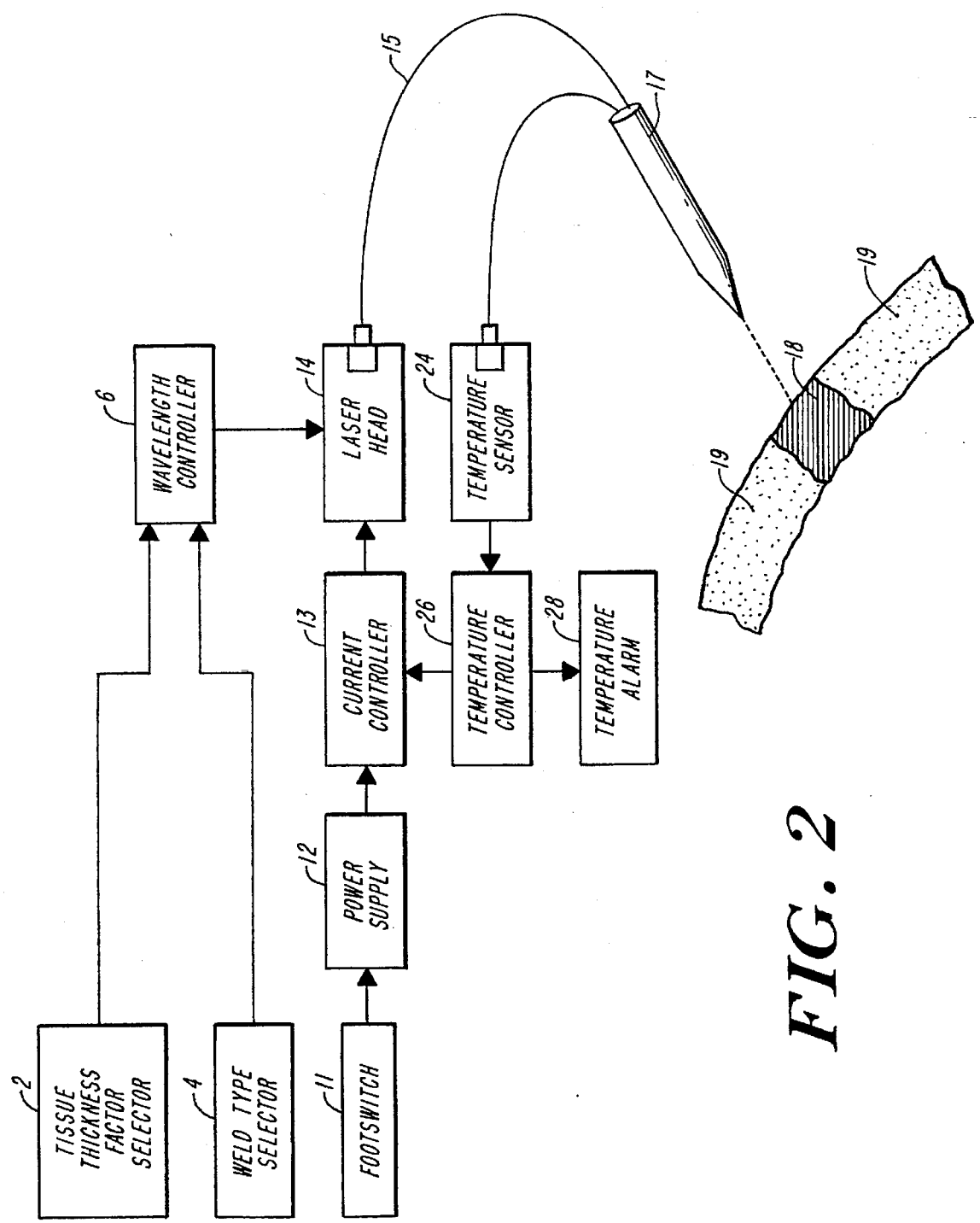
FIG. 2 shows a detailed diagram of a laser system according to the present invention.

FIG. 2 further illustrates the invention by detailing aspects disclosed in FIG. 1. System input 10 comprises tissue size selector 2 and weld type selector 4, both coupled with wavelength controller 6. Wavelength controller 6 is coupled to laser head 14. The outer diameter of subject tissue 19 is input at tissue size selector 2, and the desired form of laser weld is input at weld type selector 4. Wavelength controller 6, responsive to tissue size selector 2 and weld type selector 4, then determines and outputs to laser head 14 the wavelength at which approximately 60% or more of the laser energy will be absorbed by subject tissue 19 at the preset thickness.

The laser welding system advantageously allows matching of the laser wavelength to the thickness of subject tissue 19. By matching the laser's wavelength, and its associated penetration depth, to a particular tissue depth substantially all of the laser energy is absorbed by the subject tissue. This results in increased weld strength, more uniform welds, and decreased damage to the surrounding and target tissues.

As shown in FIG. 2, wavelength controller 6 may match the wavelength of the coherent light beam in response to the depth of subject tissue 19, as determined by tissue size selector 2 and weld type selector 4. For example, tissue size selector 2 may communicate to wavelength controller 6 the size, or outer diameter, of subject tissue 19. In addition, weld type selector 4 may communicate to wavelength controller 6 the types of tissues being welded together, i.e. vein to vein, artery to vein, or artery to artery. Given the outer diameter of a vascular tissue, and the vascular tissue types undergoing laser welding, wavelength controller 6 then determines the relative thickness of subject tissue 19 and the corresponding wavelength for achieving full absorption.

In the above example, wavelength controller 6 can determine the relative depth of subject tissue 19 in the weld zone according to known relationships between the outer diameter of vascular tissue and the thickness of vascular tissue walls. Generally, the ratio between wall thickness of an artery and the outer diameter of an artery is 1:10; and the ratio between the wall thickness of a vein and the outer diameter of a vein is 1:20. Thus, when the laser welds an artery to an artery, the depth of subject tissue 19 is one-tenth the outer diameter of subject tissue 19 input at tissue size selector 2; and when the laser welds a vein to a vein, the depth of subject tissue 19 is one-twentieth the outer diameter of subject tissue 19. In the particular case when an artery is welded to a vein, the relative depth of subject tissue 19 is defined as one-twentieth the outer diameter of the vein undergoing welding.

An alternative method for determining the thickness of arterial tissue involves measuring the outer diameter of the vessel and intraluminally placing a polyethylene tube of known diameter into the vessel. The difference between the measured outer diameter and the polyethylene tube yields a thickness of the vessel wall. The diameter and thickness at physiological pressure may be derived from a measurement of the outer vessel diameter at the appropriate pressure, from which the vessel thickness is calculated based on the conservation of wall volume, and the dimensions obtained from video measurements with the polyethylene sizing tube. Video measurements may be obtained using a Video-tracked Motion Analyzer, such as the one manufactured by Motion Analysis Corporation of Santa Rosa, Calif.

Laser source 20 comprises footswitch 11 coupled to power supply 12, coupled to current controller 13, coupled to laser head 14. Footswitch 11 provides manual control of power supply 12, which in turn controls current source 13 and laser head 14. When footswitch 11 is depressed, the laser generates a coherent light beam at a wavelength determined by wavelength controller 6. When footswitch 11 is released, no laser beam is generated.

According to one aspect of this invention, laser head 14 produces a coherent light beam with a wavelength centered at 1.9 μm. Preferably, the wavelength of coherent light produced by laser head 14 is also tunable between 1.85 μm and 1.91 μm to allow for matching of the laser penetration depth to tissues of differing thickness. This may be accomplished according to a further embodiment wherein laser head 14 constitutes a laser diode. In this embodiment, wavelength controller 6 tunes the wavelength of coherent light produced by laser head 14 by manipulating the temperature of the laser diode substrate. In particular, for every degree Centigrade that the temperature of the substrate varies, the wavelength varies 0.6 nm. Alternatively, the wavelength may be tuned by selectively filtering the light, as exemplified by a diffractive grating.

In an experimental module, a Raman shifted Nd:YAG laser as disclosed in U.S. Pat. No. 5,180,378, and incorporated herein by reference, was used as a laser diode source. The 1.9 μm light beam produced in the experimental module had a pulse duration of 60 nanoseconds at up to 2 to 3 kHz frequency, ranged in power from 120 to 250 mW.

Delivery system 40 comprises flexible optical fiber 15, probe 17, and preferably bonding agent 18. The coherent light beam output from laser head 14 is focused on the first end of optical fiber 15 and exits at the second end of fiber 15. The second end of optical fiber 15 is surrounded by probe 17. Use of optical fiber 15 with probe 17 advantageously allows easy maneuverability of the light beam in and around subject tissue 19. Typically in practice, probe 17 is held approximately 1 mm from and substantially perpendicular to subject tissue 19.

According to one aspect of this invention, the abutting ends of tissue sections being welded together are coated with bonding agent 18 prior to lasing. Bonding agent 18 comprises a protein, typically obtained from the patient's blood, suspended in water. The protein contained in bonding agent 18 is cross linked by the laser radiation in a manner similar to the cross-linking of proteins in subject tissue 19, thus acting as a glue or solder for holding the abutting ends of the tissue sections together and for increasing weld strength.

Temperature Feedback Block 30 comprises temperature sensor 24, temperature controller 26, and temperature alarm 28. Temperature sensor 24 is coupled to temperature controller 26, which is in turn coupled to both temperature alarm 28 and current controller 13. Temperature sensor 24 determines tissue temperature by interpreting data it receives from probe 17, and then relays this information to temperature controller 26. Temperature controller 26 determines whether to increase or decrease the temperature at subject tissue 19 based upon one or more of the following factors: detected tissue temperature, tissue thickness, weld type, energy and wavelength of the laser, rate of heat transfer to the environment, and the desired temperature or temperature range of tissue 19.

When temperature controller 26 identifies a tissue temperature exceeding the desired temperature by a predetermined amount, temperature controller 26 forces current controller 13 to reduce the current driving laser head 14, thereby reducing the energy output by laser head 14. This reduction in the energy impacting tissue 19 allows tissue temperature to fall. Alternatively, when the tissue temperature falls below the desired weld temperature by a predetermined amount, controller 26 causes current controller 13 to increase the current level applied to laser head 14, thereby increasing both the energy output by laser head 14 and the tissue temperature.

Preferably, temperature controller 26 maintains laser power near a steady state value by limiting the energy input to laser head 14, thereby keeping the temperature gradient across subject tissue 19 lower than would otherwise be possible. Without this limiting feature, the energy input to laser head 14 may dramatically overshoot the steady state power levels. For example, as probe 17 scans across subject tissue 19 and encounters tissue at temperature levels below the desired welding temperature, a temperature controller without the limiting feature might steadily increase the energy to laser head 14, without limit, until the desired weld temperature was achieved.

To determine the steady state power level, probe 17 is located over an area of subject tissue 19 while temperature controller 26 adjusts the power level to reach the weld temperature. When the weld temperature is reached and substantial changes in power level cease, the laser welding system is defined as having reached a steady state and the power level is recorded as the steady state power level. A maximum power level is then determined as a function of the steady state power. Generally, the maximum power level is defined as a multiplicative of the steady state power level, and preferably the maximum power level equals the steady state level multiplied by a constant in the range of one (1) to two (2). Temperature controller 26, under the steady state embodiment, only varies the power of the coherent beam of light between the maximum power level and a minimum power level, generally zero (0). These limits on power variance enable laser head 14 to operate in conditions near to steady state conditions, thus lowering the temperature gradient across subject tissue 19.

Furthermore, controller 26 may trigger alarm 28 to emit a visual and/or audio alarm when the energy levels reach the maximum power level. The alarm communicates that the user should slow down his movement of probe 17, thus reducing the energy necessary to heat the subject tissue to the desired weld temperature. For example, alarm 28 might be triggered when the user quickly moves probe 17 across subject tissue 19, making it difficult or impossible to maintain the desired welding temperature. The alarm signal instructs the user to slow his movement of probe 17, thereby prolonging the time period during which any particular area is impacted and heated by the laser.

Prior art laser welding systems relied on various sensors to monitor the surface temperature of subject tissue 19. In the case of prior welding systems this surface temperature did not, however, accurately reflect the subsurface temperature of tissue 19. The temperature difference between the exterior and interior of the tissue was often significant and resulted from the differences between the laser penetration depth and the tissue depth. For example, in the case of $CO_2$ lasers, whose absorption depth is much less than an arterial vessel wall thickness, the temperature gradient across the tissue ranges as high as 35° Centigrade. Applicant's laser system, in comparison, advantageously heats the tissue with coherent light having an adjustable penetration depth. This allows the laser's penetration depth to be set substantially equal to the tissue depth, thereby preventing large temperature gradients between the exterior and interior of the tissue. In particular, a laser system according to Applicant's invention welds tissue together while simultaneously maintaining a temperature gradient across the tissue on the order of 10° Centigrade. This reduction in the temperature gradient across the tissue in turn allows the reasonable determination of subsurface temperature by monitoring the surface temperature of subject tissue 19.

Figure 3:
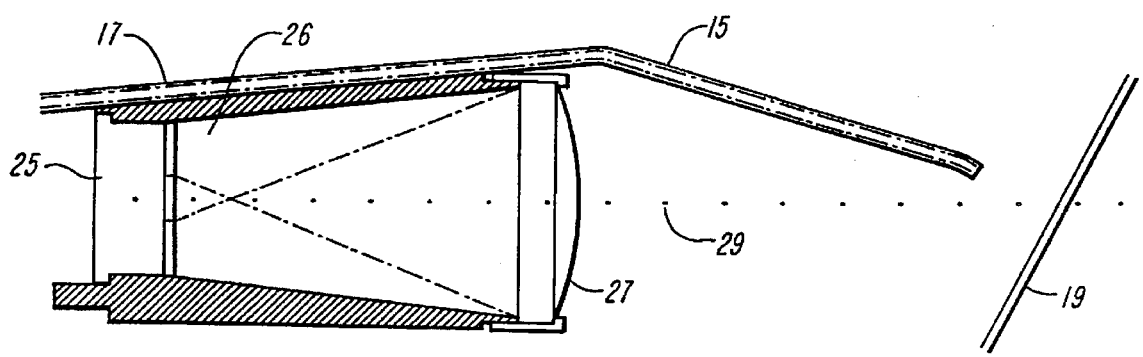
FIG. 3 shows a diagram of a laser welding probe according to the present invention.

FIG. 3 illustrates probe 17 comprising sensing head 25, aperture 26, lens 27, and optical fiber 15. Optical fiber 15 carries and emits a coherent light beam generated by laser head 14. Sensing head 25 consists of an infrared sensor, such as a thermopile detector, capable of producing an infrared sensing beam 29 for communicating with subject tissue 19. Preferably, temperature sensor 24 in conjunction with sensing head 25 is normalized and then calibrated using a known blackbody source to prevent the need to make absolute intensity measurements.

Probe 17 reduces temperature measuring errors by ensuring that the region where the coherent laser beam impacts subject tissue 19 circumscribes the viewing area of sensing head 25. As shown in FIG. 3, optical fiber 15 is mechanically connected to sensing head 25 in a manner causing overlap between the coherent laser beam and sensing beam 29, regardless of the angle optical fiber 15 is held at, relative to subject tissue 19. The size of the viewing area of sensing head 25 is controlled by aperture 26 and lens 27, either individually or in combination. For example, the viewing area of sensing head 25 may be focused with lens 27 so that the cross-sectional area of sensing beam 29 is less than the cross-sectional area of the coherent beam exiting the second end of optical fiber 15, and sensing head 25 may be mechanically aligned with optical fiber 15 so that the coherent beam and the infrared sensing beam 29 form concentric circles at the surface of tissue 19. Preferably, lens 27 is either a zinc selenide lens or a polymeric fresnel lens and the cross-section of sensing beam 29 does not exceed 0.2 $mm^2$.

By restricting the viewing area of sensing head 25 to tissue directly impacted by the coherent light beam, the laser welding system advantageously reduces error in the detected temperature resulting from background radiation and eliminates the sensitivity of temperature sensor 24 to the angular position of sensing head 25. Using these methods, the surface temperature of the tissue is held between 55°–75° C., +/–1° C.

Figure 4:
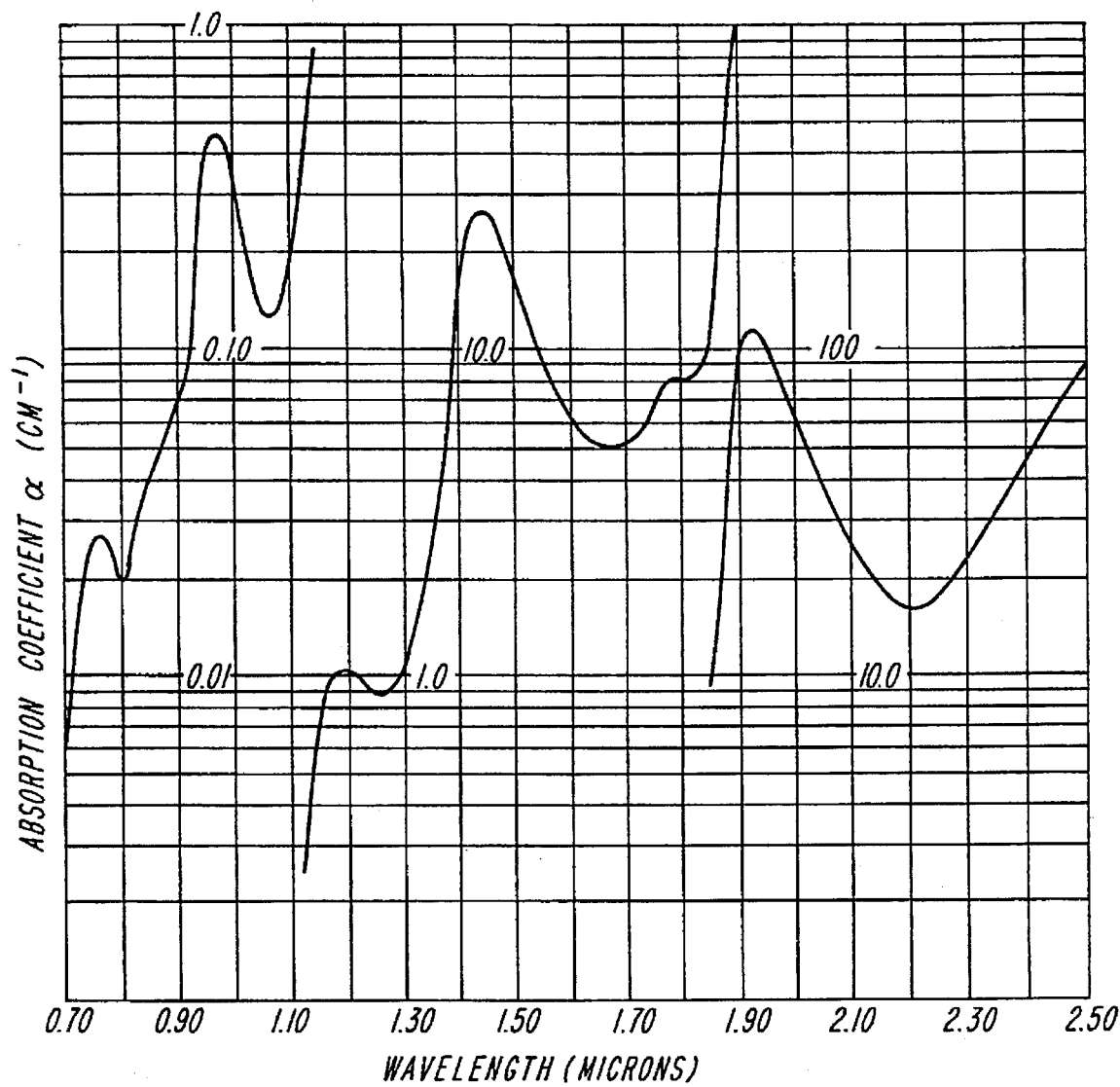
FIG. 4 shows a graph of absorption coefficient of water verses wavelength.

FIG. 4 is a graph of wavelength verses optical absorption coefficient in water. The graph of FIG. 4 also approximates the dependency of the optical absorption coefficient of various tissues On wavelength because studies show that the absorption characteristics of water and various tissue groups, such as vascular tissue, are sufficiently similar. Upon analysis, the graph shows a peak in the absorption coefficient around 1.9 µm, corresponding to an absorption depth of approximately 125 µm. Applicant's invention operates at a wavelength centered around 1.9 µm to take advantage of these absorption properties.

Further in accordance with this invention, the wavelength of the laser varies between 1.85 µm and 1.91 µm, corresponding to an optical absorption depth of 50–500 µm. In the case of arterial vessels that typically range in size from 1–3 mm, the arterial vessel walls vary between 50 µm and 250 µm. This allows a laser system according to Applicant's invention to generate a coherent beam of light at a wavelength corresponding to a specific thickness of tissue at which substantially full absorption of the laser energy occurs. This achieves significant benefits over the prior art.

For example, when the laser's optical absorption depth exceeds the tissue thickness, as in the case of an Argon laser with an absorption depth of 500 µm used in welding vascular tissue whose wall thickness ranges from 50–250 µm, the tissue only absorbs a fraction of the laser energy. This creates a need for higher laser intensities and longer exposure time to attain a suitable fusion temperature, and potentially damages surrounding tissue with the energy not absorbed by the subject tissue.

When the laser's optical absorption depth is less than the tissue thickness, as in the case of a $CO_2$ laser with an absorption depth of 20 µm used in welding vascular tissue, the laser energy is only deposited superficially on the outer tissue walls. The heat generated on the tissue exterior must conduct to the tissue interior to create a successful tissue weld. However, to heat the outer walls to a temperature sufficient to cause this heat flux, the laser intensity must be increased to a point where it causes dehydration and damage of the outer tissue walls. The resulting dehydrated tissue exhibits partial insulating characteristics that thwart attempts to successfully heat the interior of the tissue and thereby cause further reduction of internal heating and higher surface temperature. As a result, excessive surface damage may occur before the subject tissue is ever sufficiently heated to cause fusion.

Matching the laser penetration depth to the tissue thickness also obtains increased weld strength and a more uniform weld. Applicant performed experiments involving laser welding of various diameter arteriotomies on the femoral arteries and abdominal aortas of CD Fisher rats and New Zealand White Rabbits demonstrating this principle. In the experiment, vessel thickness ranged between 42 μm to 275 μm, while the diameters ranged between 0.65 mm to 2.5 mm. The 1.9 μm wavelength was generated from a Nd:YAG laser via an intracavity Raman conversion scheme. Power used was between 120 to 250 mW, delivered through a silica optical fiber at a linear rate of 0.2 mm per sec. The results of the experiment, as illustrated below in Table 1, show that a weld fashioned according to Applicant's invention achieved a weld strength at least twice as strong as those obtained using other lasing techniques.

TABLE 1

| Laser | Weld Strength ($10^6$ dynes/cm$^2$) |
| --- | --- |
| 1.9 μm laser | 4 |
| Argon laser | 2 |
| Diode laser with dye enhanced absorption | 2 |
| $CO_2$ laser | 1–2 |

The invention being thus disclosed and described in connection with the illustrated embodiments, variations and modifications thereof will occur to those skilled in the art, and are intended to be included within the scope of the invention, as defined by the claims appended hereto.

What is claimed is:

1. Apparatus for performing laser surgery to weld tissue of predetermined thickness comprising,
    a laser source producing a beam of coherent light at a center wavelength of 1.9 μm impinging on said tissue
    means for varying said laser source wavelength, such that said wavelength is at a value corresponding to substantially full absorption of said light entirely throughout said predetermined thickness of said tissue,
    temperature sensing means for sensing the temperature at the surface of said tissue to determine the temperature for substantially the entire thickness of said tissue when said laser beam is impinging on said tissue,
    means for controlling the energy of said laser beam in response to said sensed temperature for maintaining said sensed temperature below a predetermined tissue temperature.

2. Apparatus for performing laser surgery to weld tissue of predetermined thickness comprising,
    a laser source producing a beam of coherent light at a center wavelength of 1.9 μm impinging on said tissue
    means for varying said laser source wavelength, such that said wavelength is at a value corresponding to substantially full absorption of said light entirely throughout said predetermined thickness of said tissue,
    temperature sensing means for sensing the temperature at the surface of said tissue to determine the temperature for substantially the entire thickness of said tissue when said laser beam is impinging on said tissue,
    means for controlling the energy of said laser beam in response to said sensed temperature for maintaining said sensed temperature within a specified range of tissue temperature.

3. Apparatus in accordance with either of claims 1 or 2 wherein said laser source is a laser diode.

4. Apparatus in accordance with either claims 1 or 2 wherein said temperature sensing means includes an infrared sensing beam, said temperature sensing means containing a lens for focusing said sensing beam.

5. Apparatus in accordance with claim 4 wherein said lens is selected from the group consisting of polymeric fresnel lenses, and zinc-selenide lenses.

6. Apparatus in accordance with claim 4 including a means for aligning said sensing beam, such that said beam of coherent light circumscribes said infrared sensing beam at a surface of the tissue.

7. Apparatus in accordance with claims 1 or 2 wherein said means for controlling the energy of said beam of coherent light includes a steady state means for maintaining the energy of said beam of coherent light between a minimum power level and a maximum power level, such that said laser welding apparatus operates substantially at a steady state power level.

8. Apparatus in accordance with claim 7 including an alarm means for indicating when the energy of said beam of coherent light reaches said maximum power level.

9. Apparatus in accordance with claims 1 or 2 wherein said means for varying said laser source wavelength varies the wavelength of said beam of coherent light between 1.85 and 1.91 μm.

10. An apparatus in accordance with claims 1 or 2 wherein the imaging area of said beam of coherent light is less than 0.5 mm$^2$.

11. Method for performing laser surgery to weld together at least first and second sections of tissue of specific thickness comprising the steps of,
    producing a beam of coherent light controlled to be at a specific wavelength and directing said beam onto said tissue, wherein said specific wavelength is controlled to a value corresponding to substantially full absorption of said light entirely throughout said predetermined the thickness of said tissue,
    sensing the temperature at the surface of sand tissue to determine the temperature for substantially the entire thickness of tissue when said beam is directed onto said tissue, and
    controlling the energy of said beam in response to said sensed temperature to maintain said sensed temperature substantially at a specific value.

12. Method in accordance with claim 11 further including the step of coating the abutting ends of said first and said second tissue sections with a bonding agent.

13. Method in accordance with claim 11 wherein said beam producing step further includes the step of controlling the specific wavelength to a value corresponding to substantially full absorption of said light within said tissue coated with a bonding agent.

14. Method in accordance with claim 11 wherein said temperature sensing step further includes
    generating an infrared sensing beam for communicating with the first tissue section, and
    regulating the cross-section of said sensing beam.

15. Method in accordance with claim 14 wherein said sensing beam is regulated with a lens.

16. Method in accordance with claim 14 further including the step of aligning said infrared sensing beam with said coherent light beam, so that said coherent light beam circumscribes said sensing beam at a surface of said tissue.

17. Method in accordance with claim 11 further including determining a steady state energy level at which the temperature of said tissue remains substantially constant, calculating a maximum energy level and a minimum energy level as a function of said steady state energy level, and maintaining the energy of said beam of coherent light between said minimum energy level and said maximum energy level.

18. Method in accordance with claim 17 wherein said beam of coherent light is moved at a controlled rate with respect to said tissue, said controlled rate being reduced to maintain said energy of the beam of coherent light below said maximum energy level.

19. Method in accordance with claims 17 further including the step of triggering an alarm when the energy of said beam of coherent light reaches said maximum energy level.

20. Method in accordance with claim 11 wherein said wavelength of the beam of coherent light produced varies between 1.85 and 1.91 μm.

* * * * *